United States Patent [19]
Southwick et al.

[11] Patent Number: 4,974,609
[45] Date of Patent: Dec. 4, 1990

[54] TOBACCO FLAVORANTS

[75] Inventors: Everett W. Southwick, Richmond; John B. Paine, III, Midlothian, both of Va.

[73] Assignee: Philip Morris Incorporated, New York, N.Y.

[21] Appl. No.: 897,775

[22] Filed: Aug. 18, 1986

[51] Int. Cl.$^5$ .......................... A24B 3/12; A24B 15/40
[52] U.S. Cl. ..................................................... 131/277
[58] Field of Search .............................. 131/278, 277

[56] References Cited

U.S. PATENT DOCUMENTS

| | | |
|---|---|---|
| 3,529,602 | 9/1970 | Hind et al. |
| 3,703,177 | 11/1972 | Hind et al. |
| 3,796,222 | 3/1974 | Deszyck |
| 3,895,034 | 7/1975 | Winn et al. |
| 3,940,421 | 2/1976 | Razdan et al. |
| 3,946,111 | 3/1976 | Winn et al. |
| 4,019,521 | 4/1977 | Briskin |
| 4,028,373 | 6/1977 | Hromatka et al. |
| 4,079,742 | 3/1978 | Rainer et al. |

FOREIGN PATENT DOCUMENTS

| | | |
|---|---|---|
| 2615885 | 10/1977 | Fed. Rep. of Germany |
| 2700215 | 7/1978 | Fed. Rep. of Germany |

OTHER PUBLICATIONS

Woodward et al., *J. Am. Chem. Soc.*, 68, 2229–2235 (1946), "Tetrahydrothiophene Derivatives".
Hramatka et al., *Monatshaefte fuer Chemie*, 104, 1520–1525 (1973), "Mechanism of Dieckmann Reaction . . .".
Henrio et al., *Bull. Soc. Chim. Fr.*, (1–2), 265–272 (1976), "Syntheses Using 2-Acetyl and 2-Formyl-3-Hydroxythiophene and Selenophene".
Paulmier et al., *Bull. Soc. Chim. Fr.*, (7–8), 2434–2441 (1973), "Synthesis and Chemical Properties of Carbonylated and Hydroxylated Thiophenes and Selenophenes".
Roussel–Perin et al., *C.R. Acad. Sc. Paris*, 261, 464–467 (1965), "New Synthesis of Thiophenopyrones".
Henrio et al., *C.R. Acad. Sc. Paris*, 278, 125–128 (1974), "Synthesis and Chemical Properties of Variously Substituted 3-Hydroxythiophene and Selenophene".

*Primary Examiner*—V. Millin
*Attorney, Agent, or Firm*—Charles B. Smith; W. Edward Bailey; Emily A. Evans

[57] ABSTRACT

A smoking composition comprising an admixture of (1) combustible filler selected from natural tobacco, reconstituted tobacco, non-tobacco substitutes, and mixtures thereof, and (2) between about 0.00001 and 2 percent, by weight of the composition of a flavorant selected from the group consisting of compounds of the formulae wherein $R^1$, $R^2$, $R^3$, $R^6$, and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl and substituted benzyl, wherein the substituted phenyl and substituted benzyl are substituted with one or more substituents, each of said substituents being independently selected from the group consisting of $C_1$ to $C_6$ alkyl, methoxy and hydroxy.

16 Claims, No Drawings

TOBACCO FLAVORANTS

The present invention relates to a natural or synthetic tobacco composition having improved aroma and flavor.

Flavor and aroma are perhaps the most significant factors in a consumer's selection of a smokeable tobacco product. Manufacturers have achieved a desired flavor and aroma by blending various domestic and oriental tobaccos each of which contributes its own characteristic aroma and flavor during smoking. In addition, a variety of flavorants have been employed to modify available tobaccos to impart organoleptic characteristics of less readily available or more expensive tobaccos, or to impart distinct, new organoleptic properties.

More recently, efforts have been devoted to substituting synthetic flavorants for the natural extracts, which may be difficult to obtain, expensive or of variable composition.

It is an object of the present invention to provide for enhancing or otherwise improving the flavor and aroma of certain domestic, oriental, reconstituted or synthetic tobaccos and blends thereof which may be deficient in flavor or aroma.

Further and additional objects and advantages of the present invention will appear from the following description and the appended claims.

The present invention relates to a smoking composition comprising an admixture of a combustible filler selected from natural tobacco, reconstituted tobacco and nontobacco substitutes for tobacco, and an effective amount (preferably, between about 0.00001 and 2 weight percent, based on the total weight of filler) of a flavorant selected from the group consisting of compounds of the formulae XI and XX,

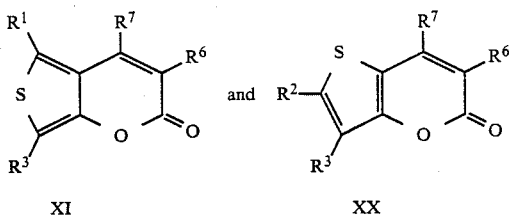

wherein $R^1$, $R^2$, $R^3$, $R^6$, and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl and substituted benzyl, wherein the substituted phenyl and the substituted benzyl are substituted with one or more substituents (preferably, one to three substituents), each of said substituents being independently selected from the group consisting of $C_1$ to $C_6$ alkyl, methoxy and hydroxy. Preferably, $R^1$, $R^2$, $R^3$, $R^6$ and $R^7$ are independently selected from the group consisting of hydrogen and $C_1$ to $C_4$ alkyl (e.g., methyl, ethyl, propyl, isopropyl and tert-butyl). It is also preferred that the foregoing compounds of the formulae XI and XX have molecular weights no greater than about 300. Thus, they will be sufficiently volatile to be volatilized when the composition is smoked. The present invention also relates to a method of improving the flavor and aroma of a tobacco or synthetic tobacco product comprising adding thereto a flavorant of the formula XI or XX.

As used herein, unless indicated otherwise, the term effective amount, as applied to a flavorant of the present invention, shall mean an amount that is effective to enhance the flavor or aroma of a smoking composition to at least some extent.

As used herein, unless indicated otherwise, the term alkyl includes both linear and branched alkyl groups.

Many of the flavorants and intermediates of the present invention can exist as various stereoisomers and optical isomers, and mixtures thereof. Unless indicated otherwise, all such isomers are included in the present invention.

Another embodiment of the present invention relates to a compound of the formula XI or XX wherein $R^1$, $R^2$, $R^3$, $R^6$, and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl and substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy, with the proviso that in the compound of the formula XX at least one of $R^2$, $R^3$, $R^6$ and $R^7$ is other than hydrogen. Such compounds are useful as flavorants in the smoking compositions of the present invention.

The present invention also relates to a compound of the formula XI or XX wherein $R^1$, $R^2$, $R^3$, $R^6$ and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; —C≡N; phenyl; benzyl; substituted phenyl; substituted benzyl; wherein the substituted phenyl and substituted benzyl are substituted with one or more substituents (preferably, one to three substituents), each of said substituents being independently selected from the group consisting of $C_1$ to $C_6$ alkyl, methoxy and hydroxy; $COOR^8$, wherein $R^8$ is selected from the group consisting of hydrogen, $C_1$ to $C_6$ alkyl, $C_3$ to $C_{12}$ cycloalkyl, benzyl, phenyl, substituted phenyl and substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy; $—CONR^9R^{10}$, wherein $R^9$ and are independently selected from the group consisting of hydrogen, $C_1$ to $C_6$ alkyl, $C_3$ to $C_{12}$ cycloalkyl, $C_1$ to $C_6$ alkoxy-$C_1$ to $C_6$ alkyl, phenyl, benzyl, substituted phenyl and substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy, or $R^9$ and $R^{10}$ taken together with the nitrogen to which they are attached form an N-methyl piperazino, morpholino, piperidino, or pyrrolidino ring;

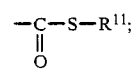

$—COR^{12}$; $—CHO$;

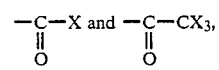

wherein X is halogen, and wherein $R^{11}$ and $R^{12}$ are independently selected from the group consisting of $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl and substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy; with the proviso that in a compound of the formula XI at least one of $R^1$, $R^3$, $R^6$ and $R^7$ is an amide, a nitrile, a carboxylic acid, a carboxylic acid ester, or a salt of a carboxylic acid (e.g., the sodium, potassium, magnesium or calcium salt), and with the provisos that in a compound of the formula XX at least one of $R^2$, $R^3$, $R^6$ and $R^7$ is an amide, a nitrile, a carboxylic acid, a carboxylic acid ester, or a salt of a carboxylic acid (e.g., the sodium, potassium, magnesium or calcium salt), and that $R^6$ cannot be —COOH or C≡N or $CONH_2$ when $R^2$, $R^3$ and $R^7$ are hydrogen. Such compounds are useful intermediates in the preparation of the aforementioned flavorants.

The present invention also relates to a compound selected from the group consisting of compounds of the formulae VIII, IX, X, XVIII and XIX,

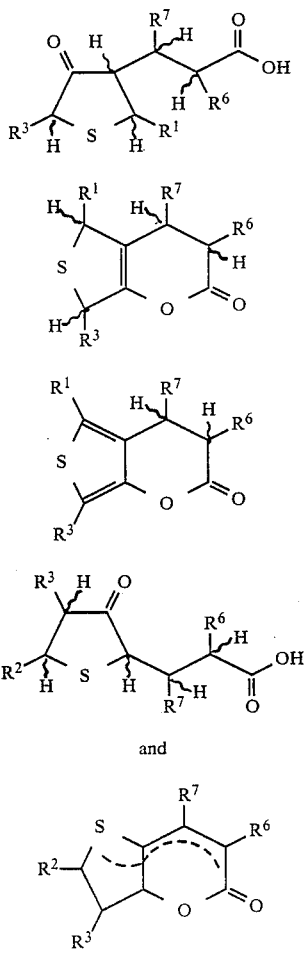

wherein the broken line indicates that one double bond is present in the formula, and wherein $R^1$, $R^2$, $R^3$, $R^6$ and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl; substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy; —C≡N; $COOR^8$, wherein $R^8$ is selected from the group consisting of $C_1$ to $C_6$ alkyl, $C_1$ to $C_6$ alkoxy-$C_1$ to $C_6$ alkyl, $C_3$ to $C_{12}$ cycloalkyl, benzyl, phenyl, substituted phenyl, substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy; —$CONR^9R^{10}$, wherein $R^9$ and $R^{10}$ are independently selected from the group consisting of hydrogen, $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy, or $R^9$ and $R^{10}$ taken together with the nitrogen to which they are attached form an N-methyl piperazino, morpholino, piperidino, or pyrrolidino ring;

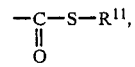

—$COR^{12}$, —CHO,

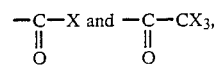

wherein X is halogen, and wherein $R^{11}$ and $R^{12}$ are independently selected from $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, and substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy. Such compounds are also useful intermediates in the preparation of the aforementioned flavorants.

The present invention also relates to compounds of the formulae XXI and XXII,

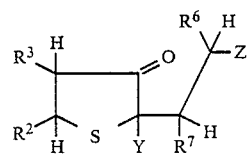

and

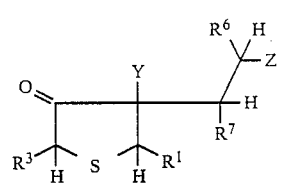

wherein $R^1$, $R^2$, $R^3$, $R^6$ and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl and substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy; —C≡N; $COOR^8$ wherein $R^8$ is selected from the group consisting of $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy; —$CONR^9R^{10}$, wherein $R^9$ and $R^{10}$ are independently selected from the group consisting of hydrogen, $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy, or $R^9$ and $R^{10}$ taken together with the nitrogen to which they are attached form an N-methyl piperazino, morpholino, piperidino, or pyrrolidino ring;

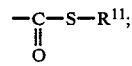

—$COR^{12}$; —CHO;

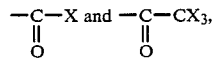

wherein X is halogen, and wherein $R^{11}$ and are independently selected from $C_1$ to $C_6$ alkyl, $C_1$ to $C_6$ alkoxy$C_1$ $C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy, and wherein Z and Y are independently selected from the group consisting of —C≡N, —$COOR^{13}$, —$CONR^{14}R^{15}$, wherein $R^{13}$, $R^{14}$ and $R^{15}$ are independently selected from the group consisting of hydrogen, $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents (preferably, one to three substituents), each of said substituents being independently selected from the group consisting of $C_1$ to $C_6$ alkyl, methoxy and hydroxy, or $R^{14}$ and $R^{15}$ taken together with the nitrogen to which they are attached form an N-methyl piperazino, morpholino, piperidino, or pyrrolidino ring.

The foregoing compounds of the formulae XXI and XXII are useful intermediates in preparing the flavorants used in the compositions of the present invention. Similar compounds of the formulae XXI and XXII are useful in preparing other flavorants.

Compounds of the formulae XXI and XXII may be prepared by alkylation (via a Michael addition) of the corresponding compound of the formula XXIII and XXIV, respectively,

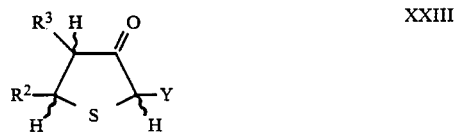

XXIII

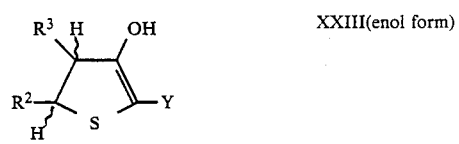

XXIII(enol form)

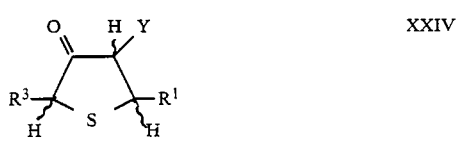

XXIV and

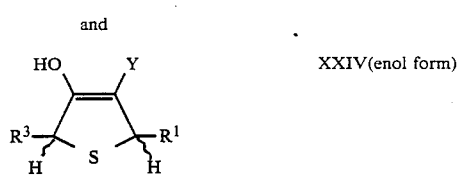

XXIV(enol form)

wherein $R^1$, $R^2$, $R^3$ and Y are as defined for formulae XXI and XXII.

PREPARATION OF FLAVORANTS

The following reaction schemes illustrate the preparation of the flavorants used in the compositions of the present invention.

Scheme 1

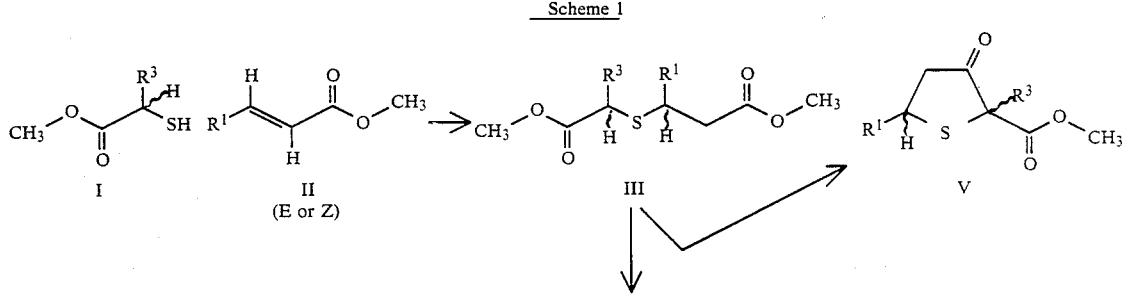

-continued
Scheme 1
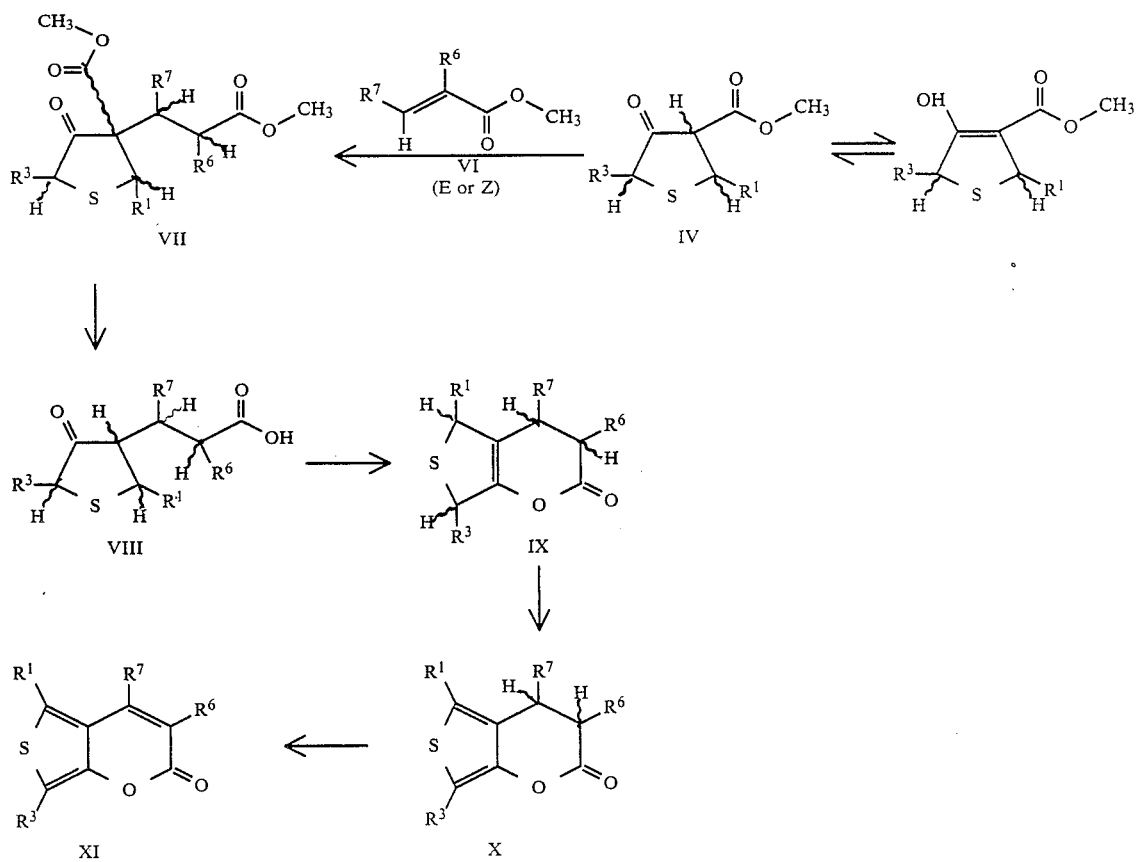
Scheme 2
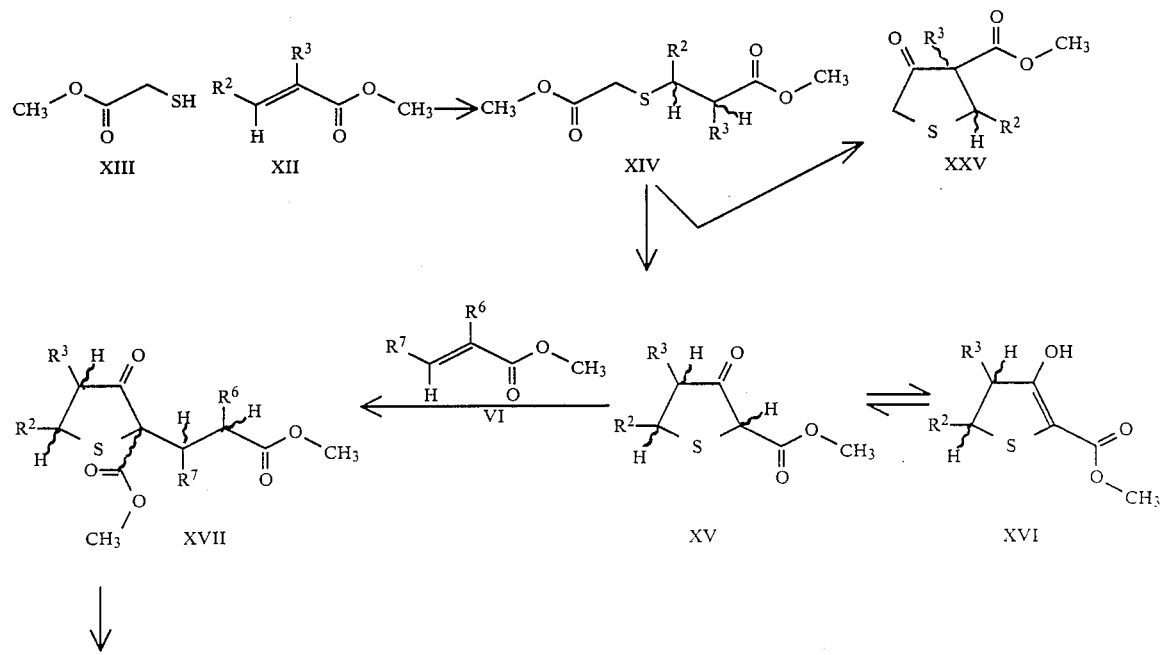

-continued
Scheme 2

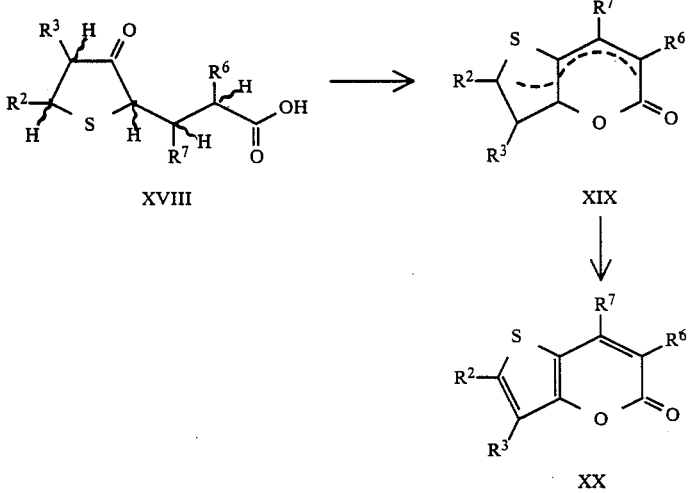

As shown in Scheme 1, an acrylate of the formula II is slowly added to a (cooled) mixture of a thioglycolate ester of the formula I and a base under an inert atmosphere to produce a compound of the formula III. The base is preferably a tertiary amine, such as triethylamine, that will not add to acrylate esters in Michael fashion or react with the ester function by aminolysis. The solvent is preferably one that may function as a source of protons so that it will help suppress potential anionic polymerization of the acrylate. Methanol is a preferred solvent for use with methyl esters to avoid possible transesterification.

The compound of the formula III is treated with 2 to 3 equivalents of 30% sodium methoxide in methanol at reflux (about 65° C.) to obtain the thermodynamic product IV as the sodium salt, along with acrylate and thioglycolate sulfide salt resulting from competing retro-Michael cleavage of the diester. If $R^3$ is hydrogen, some unstable byproduct V will also be obtained (as the sodium salt). An aqueous alkaline workup at 0° C. ensures the destruction of unstable byproduct V, if present, and allows IV to be obtained in isomerically pure form, after acidification of the reaction mixture.

The β-ketoester IV and an acrylate of the formula VI are allowed to stand at room temperature in an aprotic solvent, such as dichloromethane, containing a basic catalyst (preferably, triethylamine). Preferably, the mixture is shielded by an inert atmosphere, such as nitrogen or argon, to minimize oxidation of the β-ketoester. After about 3 to 4 days, the solvent, catalyst and excess reagent are removed by evaporation under reduced pressure.

The product VII is rinsed in ethyl acetehexane with dilute aqueous acid (e.g., HCl) in order to remove residual catalyst and salts and is then subjected to vacuum distillation.

Compound VII is then boiled in an aqueous acetic acid solution of a strong acid (preferably hydrochloric acid) to form a compound of the formula VIII. The reaction is monitored by following evolution of carbon dioxide from the decarboxylating β-ketoacid and the reaction mixture is refluxed until such evolution ceases.

The compound of the formula VIII is then dehydrated in the presence of a strong acid catalyst or an acid source to form the compound of the formula IX, preferably using a moderate excess of acetic anhydride as the dehydrating agent, and preferably under an inert atmosphere. The preferred catalyst is trifluoroacetic acid. Other strong acid catalysts include p-toluenesulfonic acid, sulfuric acid, phosphoric acid, boron trifluoride and zinc chloride. Acid sources include acetyl chloride and acetyl bromide. Generally, any inert solvent may be used. However, boiling toluene (bp 110° C. or less when it forms an azeotrope with acetic acid) is preferred.

The compound of the formula IX is oxidized to give the compound of the formula X. DDQ (2,3-dichloro-5,6-dicyano-1,4-benzoquinone) in $C_2Cl_2$ or benzene is the preferred oxidant. Other oxidants, such as sulfuryl chloride ($SO_2Cl_2$) in $CH_2Cl_2$ at low temperature ($-50°$ C. to $+10°$ C.), or molten sulfur (150° C.) may also be used. However, $SO_2Cl_2$ is disadvantageous because it results in some chlorination of the resulting thiophene ring and molten sulfur is disadvantageous because the final product may polymerize in the presence of molten sulfur. Other oxidants may be substituted for DDQ. Such oxidants include ortho-chloranil and other high potential quinones.

The compound of the formula X may be oxidized to the compound of the formula XI by fusion with DDQ at 150° C. However, severe losses to polymerization occur, and it is difficult to extract the product from the resulting tars. Better yields are obtained using DDQ as the oxidizing agent but using a solvent such as orthodichlorobenzene. Other oxidants may be substituted for DDQ. Such oxidants include ortho-chloranil and other high potential quinones. Other solvents that may be used are meta- and paradichlorobenzene, chlorobenzene, ortho-, meta-, parachlorotoluene, and bromobenzene. Benzene-type solvents which form charge-transfer complexes with DDQ (generally causing a color-change from yellow to orange, brown or red) are usually unsatisfactory. Ortho-dichlorobenzene gives no such complex with DDQ (a yellow solution results). Benzene and p-dioxane, the usual DDQ solvents cited in the literature, are particularly unsatisfactory.

Scheme 2 illustrates the preparation of compounds of the formula XX. These compounds are prepared using a method similar to that described above with respect to Scheme 1. However, one difference is that in preparing the compound of the formula XV from the compound of the formula XIV, the reaction temperature is maintained at 0° C. in order to obtain the kinetic product XV rather than the thermodynamic product, XXV (when $R^3$ is H).

Another difference between the procedure described in Scheme 1 and the procedure described in Scheme 2 is that when the compound of formula IX is prepared from the compound of formula VIII, only one isomer is formed of the enol-lactone with the double bond located along the ring-fusion; but that when the compound of formula XIX is prepared from the compound of formula XVIII, a complex mixture of double bond isomers is obtained. This mixture can be dehydrogenated smoothly with two equivalents of oxidant under mild conditions (e.g., DDQ in refluxing $CH_2C_2$, while being replaced by benzene) to give the compound of formula XX as the ultimate product so that separation of the isomers XIX is unnecessary. Other oxidants may be substituted for DDQ. Such oxidants include orthochloranil and other high potential quinones.

PREPARATION OF TOBACCO COMPOSITIONS

In the practice of the present invention, flavorant is added to tobacco or to a tobacco substitute or applied to a product comprising tobacco or a tobacco substitute or its component parts to modify or enhance the flavor thereof. The present invention is especially useful in modifying the flavor of cigarette tobacco and or tobacco substitutes used in cigarettes, but it is also suitable for use in connection with the manufacture of pipe tobacco, cigars and other tobacco and tobacco-substitute products. The quantity of flavorant employed is not narrowly critical and can vary over a wide range. Normally, the flavorant is added in an amount to give a final concentration of from about 0.00001 to about 2 weight percent, preferably from about 0.0001 to about 2 weight percent, and more preferably from about 0.001 to about 0.1 weight percent, based on the weight of the tobacco or the tobacco substitute or mixture thereof. However, the amount used will depend upon the effect desired.

The flavoring agent of the present invention may be incorporated at any step in the processing of tobacco or tobacco substitutes. It may be applied to the individual tobacco blend components, such as the natural tobaccos, reconstituted tobacco sheet, or tobacco substitutes of natural or synthetic origin. Preferably the additive is added after aging, curing and shredding and before the tobacco is formed into cigarettes.

Furthermore, the flavoring agent of this invention may be blended with tobacco, a tobacco substitute, or a mixture thereof in any convenient manner. For example, it can be dissolved in ethanol, acetone, water, or any other suitable solvents or mixtures of solvents, or admixed with a carrier such as casing solution to form a suspension or dispersion, and the resulting combination sprayed, dipped or otherwise applied on the tobacco or injected into the tobacco or tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5 to about 5 weight percent, based on the weight of filler, and then subsequently to blend the treated filler with filler which does not contain flavorant additive. Thus, solvents such as water or volatile organic solvents, such as alcohol, glycols (e.g., propylene glycol), ether, volatile hydrocarbons or mixtures of the foregoing solvents, may be used as the carrier medium for the agent while it is applied to the tobacco. Alternatively, the agent can be blended with other additives and then mixed into the tobacco. Thus, it can be incorporated into blends normally employed to produce reconstituted tobacco sheet or tobacco substitutes of natural or synthetic origin. Inasmuch as the flavoring agent of this invention is somewhat volatile, it may also be incorporated into the filter tip, the seam paste employed for gluing the cigarette paper or the packaging material.

The term "tobacco" as used throughout this specification, unless indicated otherwise, is intended to include not only tobacco plant leaves but also other parts of the tobacco plant that are suitable for smoking.

The term "non-tobacco substitute" is meant to include smoking filler materials such as are disclosed in U.S. Pat. Nos. 3,529,602; 3,703,177; 3,796,222; 4,019,521; 4,079,742; and references cited therein. The foregoing patents are hereby incorporated herein by reference.

Illustratively, U.S. Pat. No. 3,529,602 describes a burnable sheet which may be used as a tobacco substitute, which sheet contains ingredients which include (1) a film forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or a clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or other carbohydrate material at a temperature of 150°-750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

It should be appreciated that in the art of flavor blending a variety of effects are possible from a flavorant depending on the amounts of flavorant used and the nature of the substrate. Therefore, the present invention contemplates the blending of the flavorants of formula XI and XX with other flavorants and the application of these flavor mixtures to a variety of tobacco substrates, both synthetic and natural tobaccos. The amount to be blended with the other flavorants is of course optional depending on the particular effect one is trying to achieve and the type of tobacco or tobaccos to which the mixture is added.

The following examples are further illustrative of the present invention. The reactants and other specific ingredients are presented as being typical, and various modifications can be derived in view of the foregoing disclosure within the scope of the invention.

EXAMPLE 1

Preparation of Methyl 3-[(2methoxy-2-oxoethyl)thio]propanoate (dimethyl 3-thiahexanedioate) III, $R^1=R^3=H$ or XIV, $R^2=R^3=H$ Methyl acrylate (820.67 g., 9.5327 mol) was added, over 100 min, under $N_2$, to a magnetically stirred solution of methyl thioglycolate (1007.18 g, 9.489 mol) and triethylamine (138.96 g, 192 mL, 1.373 mol) in methanol (1000 mL, plus a subsequent 239.83 g from a wash-bottle, for rinsings). After the reaction vessel became warm, the reaction vessel (a 4L heavy-wall Erlenmeyer flask) was immersed in a bucket of cold water to moderate the reaction. The reaction mixture was permitted to stand overnight and was then concentrated on a rotary evaporator. The residue was distilled in vacuo in two lots (bp 122°–131° C./1.5 torr) to yield 1804.37 g (98.9%). NMR and GC/MS data agreed with the proposed structure, which is a known compound (see R. B. Woodward and R. H. Eastman, *J. Am. Chem. Soc.*, 68, 2229–2235 (1946)).

EXAMPLE 2

Preparation of Methyl (R,S)-Tetrahydro-4-oxo-3-thiophenecarboxylate IV, $R^1=R^3=H$ Sodium methoxide (530.87 g; 9.827 moles) was transferred under $N_2$ to a 4L heavy wall Erlenmeyer flask. Methanol (1440 mL freshly distilled from magnesium methoxide) was added, and the resulting warm solution was refluxed as methyl 3-[(2-methoxy-2-oxoethyl)thio]-propanoate (597.57 g, 3.1086 moles) was added over 20 min. The reaction mixture was refluxed for a further 20 min, and was then allowed to cool overnight.

The reaction mixture (2200 mL) was poured onto crushed ice in two 4 L beakers, let stand for 7 min, and then acidified with concentrated HCl (900 mL). The resulting slurry (7 L) of crystallized product was filtered, and the solids rinsed with $H_2O$ (1 L). The filtrates were extracted once with $CH_2Cl_2$ (1 L). The $CH_2Cl_2$ extracts were washed with $H_2O$, to which $NaHCO_3$ was added until effervescence ceased. The filter-cakes were separately rinsed through the filter with $CH_2Cl_2$, and similarly treated with $NaHCO_3$. The organic phases were concentrated separately in vacuo, and the residues (286.43 g from the filter-cakes, 106.79 g from the aqueous filtrates) crystallized separately from methanol at −20° C., giving initially 151.05 g (30.33%) and 34.85 g (7.00%), respectively.

The $^{13}C$ and $^1N$ NMR data were in accord with the proposed structure, a known compound (see O. Hromatka et al. (*Monatshäfte für Chemie*, 104, 1520–1525 (1973)), and P. Rossy et al. (Ger. Offen. 2615885)), and showed it to be in tautomeric equilibrium with methyl 2,5-dihydro-4-hydroxy-3-thiophenecarboxylate.

EXAMPLE 3

Preparation of Methyl (R,S)-Tetrahydro-3-(3-methoxy-3-oxopropyl)-4-oxo-3-thiophenecarboxylate VII, $R^1=R^3=R^3=R^6=R^7=H$ A solution of methyl (R,S)-tetrahydro-4-oxo-3-thiophenecarboxylate (96.40 g, 0.6018 mol), methyl acrylate (70.7 g, 74 mL, 0.82 mol), and triethylamine (90 mL) in dichloromethane (300 mL) was allowed to stand at room temperature under nitrogen for 6 days. The solvent and excess reagents were removed (rotary evaporator, 60° C.). The oily residue was dissolved in ethyl acetate (250 mL) and hexane (250 mL), and then shaken with concentrated HCl (50 mL) in $H_2O$ (200 mL). The resulting organic phase was washed with $H_O$ (250 mL, then 200 mL), and then concentrated on a rotary evaporator, first at 55° C., then at 100° C. The residue was distilled twice (Kugelrohr, bp mostly 132°–189° C. (external)/0.58–0.70 Torr) to afford a colorless oil, 138.60 g (93.58%). $^1H$ and $^{13}C$ NMR, and GC/MS data were in accord with the proposed structure. Anal. calcd for $C_{10}H_{14}O_5S$: C, 48.77; H, 5.73; S, 13.02. Found: C, 48.53; H, 5.74; S, 12.83.

EXAMPLE 4

Preparation of (R,S)-Tetrahydro-4-oxo-3-thiophenepropanoic Acid VIII, $R^1=R^5=R^6=R^7=H$ Methyl (R,S)-tetrahydro-3-(3-methoxy-3-oxopropyl)-4-oxo-3-thiophenecarboxylate (46.81 g, 0.190 mol) was refluxed with acetic acid (400 mL), concentrated HCl (100 mL) and $H_2O$ (100 mL) until gas evolution ceased (4.5 h). The solvent was removed (rotary evaporator at 100° C.). The residual oil was dissolved in $CH_2Cl_2$, rinsed once with $H_2O$, and reconcentrated in vacuo. The residue was twice distilled (Kugelrohr) at 172°–202° C. (external)/1 Torr to yield 31.23 g (94.3%). The pale yellow viscous oil solidified on seeding. A sample for analysis was recrystallized from ethyl acetate/hexane; mp 64.0°–67.0° C. Anal. calcd. for $C_7H_{10}O_3S$: C, 48.26; H, 5.79; S, 18.40. Found: C, 48.14; H, 5.89; S, 18.83. $^{13}C$ and $^1H$ NMR, and GC/MS data were all in accord with the proposed structure.

EXAMPLE 5

Direct Preparation of (R,S)-Tetrahydro-4-oxo-3-thiophenepropanoic Acid VIII, $R^1=R^3=R^6=R^7=H$ Methyl (R,S)-tetrahydro-4-oxo-3-thiophenecarboxylate (175.49 g, 1.0955 moles), methyl acrylate (124.43 g., 130 mL, 1.4453 moles), and triethylamine (151 mL) were kept, under $N_2$, in $CH_2Cl_2$ (500 mL) solution at room temperature for 4 days. A principal mobile product was observed by TLC ($C_2Cl_2$-silica, $I_2$-vapor visualization).

The solvent was removed in vacuo, and chased with toluene (500 mL) and then acetic acid (500 mL). Minor hygroscopic crystals were removed from the toluene solution by filtration.

The crude diester was refluxed for 8 h in acetic acid (500 mL, plus rinsings)-$H_2O$ (125 mL)-concentrated HCl (100 mL). Low-boilers were removed periodically, by using a solvent still-head to both recycle and remove distillate. After 2 h, concentrated HC (100 mL) and $H_2O$ (150 mL) were added to maintain the volume.

535 mL of the solvent was removed at 1 atm and the remainder was removed with a rotary evaporator. The residue was dissolved in $CH_2Cl_2$ (500 mL) and washed with $H_2O$ (200 mL). The organic phase was concentrated in vacuo, and the residue distilled (Kugelrohr) at 170°–250° C.(external)/1–2 Torr, to yield 162.89 g (85.3%).

EXAMPLE 6

Preparation of 3,5,6,7-Tetrahydro-1H-thieno[3,4-b]pyran-5one IX, $R^\pm=R^3=R^6=R^7=H$ A toluene (100 mL) solution of (R,S)-tetrahydro-4-oxo-3-thiophenepropanoic acid (19.06 g, 0.1094 mol), acetic anydride (27.68 g, 26 mL, 0.2711 mol), and trifluoroacetic acid (8.94 g, 6.2 mL, 0.0784 mol) was refluxed under $N_2$ for 5 h. The reaction mixture was allowed to stand at room temperature under $N_2$ overnight and the solvent was then removed in vacuo (rotary evaporator). The residue was then distilled (Kugelrohr) at 111°–136° C. (external)/0.36–0.52 Torr to yield 16.33 g (95.6%). The product solidified in storage at −20° C. It is sensitive to $H_2O$, $O_2$ and light. NMR and GC/MS data were in agreement with the proposed structure. Some oxidation to the corresponding thiophene occurs if air instead of $N_2$ is used as the atmosphere for the reaction.

EXAMPLE b 7

Preparation of 6,7-Dihydro-5H-thieno[3,4-b]pyran-5-one X, $R^1=R^3=R^6=R^7=H$

A magnetically-stirred solution of 3,5,6,7-tetrahydro-1H-thieno[3,4-b]pyran-5-one (14.32 g, 0.09168 mol) in benzene (150 mL) was treated, in portions, with 2,3-dichloro-5,6-dicyano-1,4-benzoquinone (DDQ) (21.29 g, 0.09378 mol). The DDQ dissolved exothermically, giving a dark brown solution which gradually faded to orange, as the crystalline hydroquinone separated. The solids were removed by filtration and rinsed with $CH_2Cl_2$. The filtrates were concentrated in vacuo, and the residue was twice distilled (Kugelrohr) to give a mobile light orange oil. (bp > 141° C./1.8 Torr or 126°–145° C./0.55 Torr, external temperature). Yield: 11.98 g (84.7%). The product solidified upon storage under $N_2$ at −20° C. NMR and GC/MS data were in agreement with the proposed structure. The compound is sensitive to water, oxygen and light.

EXAMPLE 8

Preparation of 5H-Thieno[3,4-b]pyran-5-one XI, $R^1=R^3=R^650$ $R^6=H$ 6,7-Dihydro-5H-thieno[3,4-b]pyran-5-one (2.78 g, 18.03 mmol) and DDQ (5.48 g, 24.14 mmol) were rinsed into a 25 mL pear-shaped 14/20 flask with $CH_2Cl_2$, and heated (silicone bath). The $CH_2Cl_2$ was distilled off, the last being flushed out by $N_2$. At 145°–150° C., the condenser suddenly fogged, as a reaction seemed to occur and the reaction mixture became a dark mass. The reaction mixture was kept at 150° C. overnight and it became black and tarry.*
* Better yields may be obtained by employing boiling orthodichlorobenzene as the solvent.

The black tarry mass was leached with $CH_2Cl_2$, and ground under $CH_2Cl_2$ in a mortar. The extracts were filtered and the resulting filtrates were then concentrated in vacuo. The residue was distilled (Kugelrohr) (bp 116.5°–147 C., external/370 milliTorr) to give: Distillate, 1.09 g; undistillable residue, 0.53 g. The distillate was twice crystallized from ethanol (100%) (3 mL each crystallization) to yield 0.73 g (26.6%), mp 82.5°–85.2° C.

An analytically pure sample was obtained by silica gel chromatography, mp 85.6°–86.8° C. Anal. calcd. for $C_7H_4O_2S$: C,55.25; H,2.65; S,21.07. Found: C,54.94; H, 2.65; S,20.97. The $^1H$ and $^{13}C$ NMR data and GC/MS results were consistent with the proposed structure.

EXAMPLE 9

Direct Preparation of 5H-Thieno[3,4-b]pyran-5-one XI, $R^1=R^3=R^6=R^7=H$

A solution of (R,S)-tetrahydro-4-oxo-3-thiophenepropanoic acid (34.90 g, 0.2002 mol), acetic anhydride (55.49 g, 51.5 mL, 0.5435 mol) and trifluoroacetic acid (18.61 g, 12.7 mL, 0.1632 mol) in toluene (253 mL) was refluxed under $N_2$ for 80 min. The reaction mixture was permitted to stand overnight under $N_2$. The solvent was then removed (rotary evaporator), and the residue distilled (Kugelrohr), bp 146.5°–170.0° C. (external)/1.5 Torr to yield 30.67 g (98%).

The resulting 3,5,6,7-tetrahydro-1H-thieno[3,4-b]pyran-5-one was added, in several portions, to a magnetically stirred suspension of 2,3-dichloro-5,6-dicyano-1,4-benzoquinone (DDQ) (53.54 g, 0.2358 mol) in dichloromethane (400 mL), at room temperature, in a 1L Erlenmeyer flask. After an induction period, the mixture warmed as the color faded and the hydroquinone crystallized. The last of the starting material was rinsed in with $CH_2Cl_2$.

The hydroquinone was filtered off (sintered glass filter) and rinsed with $CH_2Cl_2$. The filtrates were concentrated on a rotary evaporator to a dark brown mobile oil.

This, and further DDQ (76.56 g, 0.3373 mol) were heated in 1,2-dichlorobenzene (350 mL) until the solvent boiled. The mixture darkened and deposited black tars, as fumes of HCl were evolved. The mixture was refluxed until TLC showed absence of 6,7-dihydro-5H-thieno[3,4-b]pyran-5-one (30 to 60 min). After being allowed to cool to room temperature, the reaction mixture was diluted with $CH_2Cl_2$ (500 mL), and was then filtered through sintered glass.

The filtrates were stirred vigorously with a solution of $Na_2S_2O_5$ (40.15 g, 0.2112 mol) in $H_2O$ (800 mL), isolated, then stirred with a solution of $Na_2CO_3$ (40.53 g, 0.3824 mol) in $H_2O$ (800 mL). The organic phase was isolated, and was then washed with $H_2O$ (800 mL). It was then concentrated on a rotary evaporator, first at 60° to 100° C. (water-aspirator) to remove $CH_2Cl_2$, then at 100° C. (oil pump) to remove the 1,2-dichlorobenzene. The residue was distilled (Kugelrohr) at 133°–217° C. (external)/0.71–0.80 Torr to yield 17.23 g (57.57% overall).

EXAMPLE 10

Preparation of Methyl (R,S)-Tetrahydro-3-oxo-b 2-thiophenecarboxylate XV, $R^2=R^3=H$ Sodium metal (24.95 g, 1.0853 g-atom) was dissolved, under $N_2$, in Mg-dried methanol (208 mL, 160.32 g). The resulting solution was cooled (ice-bath), and was stirred magnetically at 0° C. as methyl 3-[(2-methoxy-2-oxoethyl)thio]propanoate (96.28 g, 82 mL, 0.5009 mol) was added over 60 min. Methanol (10 mL) was used to rinse in the last of the diester. The thick pasty mixture was stirred with a spatula to ensure homogeneity, and was then let stand at 0° C. for 1 h, under N₂. Concentrated HCl (101 mL), diluted to 600 mL with ice, was added, and was stirred in manually and then magnetically until a mixture of an oily phase and an aqueous phase resulted. The mixture also contained a small amount of precipitated sodium chloride.

Dichloromethane (100 mL) was stirred in and the organic phase was then isolated. The aqueous phases were further extracted with CH₂Cl₂ (2×125 mL). The combined organic phases were washed with saturated aqueous NaHCO₃ (200 mL), and then concentrated in vacuo. The residue was distilled (Kugelrohr) at 110°–161° C. external/5 torr, to give 72.51 g (90.38%).

The $^1$H and $^{13}$C NMR data were in accord with the proposed structure, a known compound (see P. A. Rossy and W. Hoffmann, Ger.Offen. 27 00215 (July 13, 1978)); the corresponding enol, methyl 4,5-dihydro-3-hydroxy-2-thiophenecarboxylate could barely be detected by NMR. A slight amount (less than 5%) of the isomer, methyl (R,S)-tetrahydro-4-oxo-3-thiophenecarboxylate was present.

EXAMPLE 11

Preparation of Methyl (R,S)-Tetrahydro-2-(3-methoxy-3-oxopropyl)-3-oxo-2-thiophenecarboxylate XVII, $R^2=R^3=R^6=R^7=H$ Methyl (R,S)-tetrahydro-3-oxo-2-thiophenecarboxylate (128.40 g, 0.8016 mole if pure, containing about 12.5% of the uncyclized precursor (XIV, $R^2=R^3=H$), but unlike the product of Example 10, no XXV ($R^2=R^3=H$)), methyl acrylate (86 mL, 82.2 g., 0.955 mol), and triethylamine (76 mL, distilled from phthalic anhydride) were kept at room temperature in CH₂Cl₂ (300 mL) for 5 days. The solvent and excess reagents were removed (rotary evaporator, at 60° C., then 100° C.). The residue was dissolved in ethyl acetate (about 250 mL) and n-hexane (260 mL), and washed with conc. HCl (20 mL) in H₂O (200 mL). The resulting organic phase was washed with H₂O (500 mL), then concentrated (rotary evaporator). The residue was distilled (Kugelrohr, bp about 128°–210° C. (external)/0.52–1.4 torr) to give a main fraction of 137.89 g (69.85% nominally, estimated by $^{13}$C NMR to be at least 96% pure), and a low-boiling fraction of 29.00 g (estimated by $^{13}$C NMR to contain 12.96 g of product and 16.04 g of XIV ($R^2=R^3=H$)). Repeated Kugelrohr distillation the low boilers afforded a pure sample (bp 125°–142° C. (external)/0.6 Torr) of XVII ($R^2=R^3=R^6=R^7=H$) which was analyzed.

Anal. calcd. for C₁₀H₁₄OS: C, 48.77; H, 5.73; S, 13.02. Found: C, 48.46; H, 5.76;S, $^{13.12.}$ $^1$H and $^{13}$C NMR, and GC/MS data were consistent with the proposed structure. Corrected for impurities in the starting material and low boilers, the yield of product XVII ($R^2=R^3=R^6=R^7=H$) based upon XV/XVI ($R^2=R^3=H$) was about 87%.

EXAMPLE 12

Preparation of (R,S)-Tetrahydro-3-oxo-2-oxo-2-thiophenepropanoic Acid XVIII, $R^2=R^3=R^6=R^7=H$ Methyl (R,S)-tetrahydro-2-(3-methoxy-3-oxopropyl)-3-oxo-2-thiophenecarboxylate (49.93 g, 0.2027 mol), concentrated HCl (101 mL), H₂O (100.5 mL) and acetic acid (401 mL) were refluxed until gas evolution ceased (3 h). After the solvent was removed in vacuo, the residue was dissolved in CH₂Cl₂ (250 mL), washed with H₂O (100 mL), and recovered (rotary evaporator). The residue was distilled (Kugelrohr) twice, at 145°–190° C. (external)/1.3–1.7 Torr to yield 25.38 g (71.9%).

A sample for analysis was twice recrystallized at −20° C. from ethyl acetate-hexane, mp 50.5–53.5° C. (The compound darkened on standing.) Anal. calcd. for C₇H₁₀O₃S: C,48.26; H, 5.79; S, 18.40. Found: C, 46.50, 46.84; H, 5.75, 5.77; S, 18.03. The $^1$H and $^{13}$C NMR, and GC/MS data were consistent with the proposed structure. Another sample, purified by redistillation and stored under N₂, gave: C, 48.09; H, 5.99; S, 18.59.

EXAMPLE 13

Preparation of Tetrahydrothieno[3,2-b]pyran-5-ones XIX, $R^2=R^3=R^6=R^7=H$ (R,S)-Tetrahydro-3-oxo-2-thiophenepropanoic acid (15.83 g, 0.09087 mol), acetic anhydride (30 mL), and toluene (104 mL) were heated to boiling, and then trifluoroacetic acid (TFA) (5 mL) was added. After the reaction mixture was refluxed for 150 min, further TFA (5.3 mL) was added, and reflux was continued for one hour. The solvent was removed; 63 mL at 1 atm, and the remainder on a rotary evaporator. The residue was distilled (Kugelrohr) at 115°–170° C. (external)/0.8–1.4 Torr to yield 11.76 g (82.8%). GC/MS indicated that this was a complex mixture of double bond isomers. The mixture is believed to have contained the following isomers:

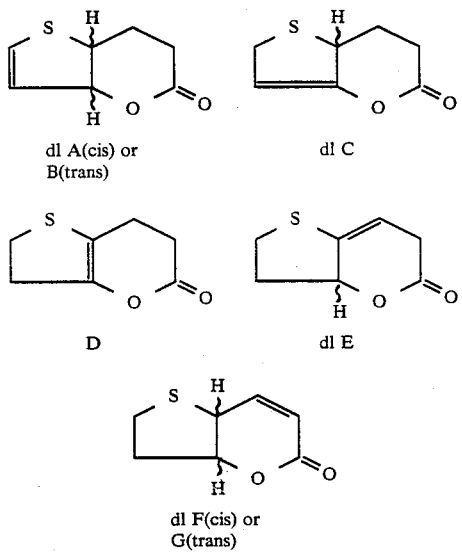

dl A(cis) or B(trans)

dl C

D dl E dl F(cis) or G(trans)

of which C, D and E tend to predominate to varying extents depending on the precise circumstances of preparation.

EXAMPLE 14

Preparation of 5H-Thieno[3,2-b]pyran-5-one XX, $R^2=R^3=R^6=R^7=H$

The mixture of tetrahydrothieno[3,2b]-pyranones XIX (11.76 g, 0.07529 mol) and 2,3-dichloro-5,6-dicyano-1,4-benzoquinone (DDQ) (40.05 g, 0.1764 mol) were suspended in CH₂ Cl₂ (100 mL), giving, with immediate reaction, a dark greenish black solution from which the hydroquinone soon began to crystallize. The mixture was refluxed and the CH₂Cl₂ was distilled off, as benzene (2 X 100 mL) was added (2 h). GC/MS indicated that the mixture, at this stage, contained four principal components: m/e (%): 154 (15.1%), 154 (4.0%), 152 (69.6%), and 156 (1.3%).

The solids were filtered off and rinsed with $CH_2Cl_2$. The filtrates were concentrated in vacuo, and twice distilled (Kugelrohr) to yield 6.56 g (57.26%). This material was recrystallized from ethanol in two crops of 4.79 g (41.81%) and 0.82 g (7.15%). The material of the first crop had a mp of 12.5°–114.5° C. after partial fusion and recrystallization at 105°–108.5° C. (indicating that the material was polymorphic). An analytically pure sample was obtained by silica gel chromatography, mp 115.5°–116.8° C. (literature mp 110° C. (see G. Henrio et al., *Bull. Soc. Chim. Fr.*, 265–272 (1976)). The $^1H$ and $^{13}C$ NMR and GC/MS data were in accord with the proposed structure. Anal. calcd for $C_7H_4O_2S$: C, 55.25; H, 2.65; S, 21.07. Found: C, 55,43; H, 2.71; S, 21.25.

EXAMPLE 15

Cigarettes treated with compound XI of Example 9, at a concentration of 200 ppm, demonstrated a sweet, dusty flavor effect when smoked. Cigarettes treated with compound XX of Example 14, at a concentration of 100 ppm, exhibited a slight fruity-vanilla note when smoked. This evaluation was performed for each compound by smoking two cigarettes which were identical in all respects with the exception that one of the two contained a homogeneous distribution of the test compound at the level of application indicated.

It will be appreciated that while embodiments of this invention are shown above, the invention is not to be limited thereto, since many modifications can be made by those skilled in the art without departing from the spirit and scope of the invention as set forth in the appended claims.

What is claimed is:

1. A smoking composition comprising an admixture of (1) combustible filler selected from natural tobacco, reconstituted tobacco, non-tobacco substitutes, and mixtures thereof, and (2) between about 0.00001 and 2 percent, by weight of the composition, of a flavorant selected from the group consisting of compounds of the formulae XI and XX,

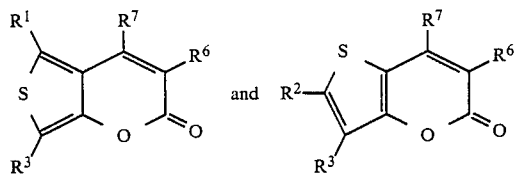

wherein $R^1$, $R^2$, $R^3$, $R^6$, and $R^7$ are independently selected from the group consisting of hydrogen, $C_1$ to $C_6$ alklyl, $C_1$ to $C_6$ alkoxy-$C_1$ to $C_6$ alkyl, $C_3$ to $C_{12}$ cycloalkyl, phenyl, benzyl, substituted phenyl and substituted benzyl, wherein the substituted phenyl and the substituted benzyl are substituted with one or more substituents, each of said substituents being independently selected from the group consisting of $C_1$ to $C_6$ alkyl, methoxy and hydroxy.

2. A smoking composition in accordance with claim 1, wherein $R^1$, $R^2$, $R^3$, $R^6$ and $R^7$ are independently selected from the group consisting of hydrogen and $C_1$ to $C_4$ alkyl.

3. A smoking composition in accordance with claim 2, wherein said compound of the formula XI is 5H-thieno[3,4-b]pyran-5-one and said compound of the formula XX is 5H-thieno[3,2-b]pyran-5-one.

4. A smoking composition in accordance with claim 1, wherein the non-tobacco substitutes are selected from pectinaceous, cellulosic and carbohydrate materials.

5. A smoking composition of claim 1 in the form of a cigarette.

6. A method for improving the flavor of a smoking composition, which method comprises incorporating into natural tobacco, reconstituted tobacco, non-tobacco substitute or mixtures thereof from about 0.00001 to about 2 percent, by weight of the composition, of a flavorant selected from the group consisting of the compounds of the formulae XI and XX,

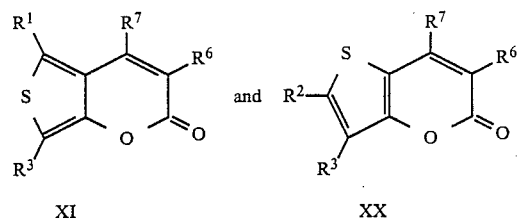

Where $R^1$, $R^2$, $R^3$, $R^6$, and $R^7$ are independently selected from the group consisting of hydrogen, $C_1$ to $C_6$ alklyl, $C_1$ to $C_6$ alkoxy-$C_1$ to $C_6$ alkyl, $C_3$ to $C_{12}$ cycloalkyl, phenyl, benzyl, substituted phenyl and substituted benzyl, wherein the substituted phenyl and the substituted benzyl are substituted with one or more substituents, each of said substituents being independently selected from the group consisting of $C_1$ to $C_6$ alkyl, methoxy and hydroxy.

7. The method of claim 6, wherein $R^1$, $R^2$, $R^3$, $R^6$ and $R^7$ are independently selected from the group consisting of hydrogen and $C_1$ to $C_4$ alkyl.

8. The method of claim 8, wherein said compound of the formula XI is 5H-thieno[3,4-b]pyran5-one and said compound of the formula XX is 5H-thieno[3,2-b]pyran-5-one.

9. The method of claim 6, wherein the amount of flavorant added to the smoking composition is from about 0.0001 to about 0.01 percent by weight of the composition.

10. A compound selected from the group consisting of compounds of the formulae Xl and XX,

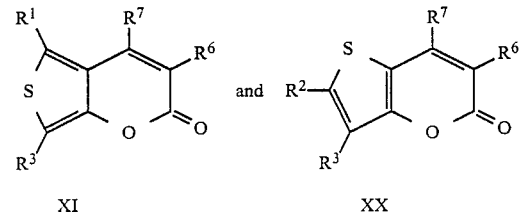

wherein $R^1$, $R^2$, $R^3$, $R^6$, and $R^7$ are independently selected from the group consisting of hydrogen, $C_1$ to $C_6$ alkyl, $C_1$ to $CH_6$ alkoxy-$C_1$ to $C_6$ alkyl, $C_3$ to $C_{12}$ cycloalkyl, phenyl, benzyl, substituted phenyl and substituted benzyl, wherein the substituted phenyl and substituted benzyl are substituted with one or more substituents, each of said substituents being independently selected from the group consisting of $C_1$ to $C_6$ alkyl, methoxy and hydroxy, with the proviso that in the compound of the formula XX at least one of $R^2$, $R^3$, $R^6$ and $R^7$ is other than hydrogen.

11. A compound according to claim 10, wherein $R^1$, $R^2$, $R^3$, $R^6$ and $R^7$ are independently selected from the group consisting of hydrogen and $C_1$ to $C_4$ alkyl.

12. A compound according to claim 11, said compound being 5H-thieno[3,4-b]pyran-5-one.

13. A compound according to claim 11, wherein three of the groups $R^2$, $R^3$, $R^6$ and $R^7$ are hydrogen and one of said groups is other than hydrogen.

14. A compound selected from the group consisting of compounds of the formulae XI and XX,

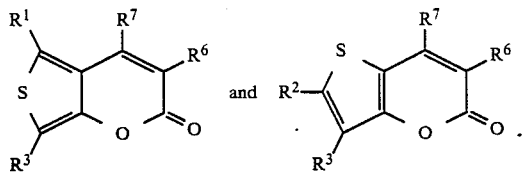

XI          XX wherein $R^1$, $R^2$, $R^3$, $R^6$ and $R^7$ are independently selected from the group consisting of: hydrogen; $C_1$ to $C_6$ alkyl; $CH_1$ to $C_6$ alkoxy-$C_1$ to $C_6$ alkyl; $C_3$ to $C_{12}$ cycloalkyl; $-C\equiv N$; phenyl; benzyl; substituted phenyl; substituted benzyl; wherein the substituted phenyl and substituted benzyl are substituted with one or more substituents, each of said substituents being independently selected from the group consisting of $C_1$ to $C_6$ alkyl, methoxy and hydroxy; $COOR^8$, wherein $R^8$ is selected from the group consisting of hydrogen, $C_1$ to $C_6$ alkyl, $C_1$ to $CH_6$ alkoxy-$C_1$ to $C_6$ alkyl, $C_3$ to $C_{12}$ cycloalkyl, benzyl, phenyl, substituted phenyl and substituted benzyl, wherein the substituted phenyl and substituted benzyl are substituted with one or more substituents, each of said substituents being independently selected from the group consisting of $C_1$ to $C_6$ alkyl, methoxy and hydroxy; $-CONR^9R^{10}$, wherein $R^9$ and $R^{10}$ are independently selected from the group consisting of hydrogen, $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl and substituted benzyl, wherein the substituted phenyl and substituted benzyl are substituted with one or more substituents, each of said substituents being independently selected from the group consisting of $C_1$ to $C_6$ alkyl, methoxy and hydroxy, or $R^9$ and $R^{10}$ taken together with the nitrogen to which they are attached form an N-methyl piperazino, morpholino, piperidino, or pyrrolidino ring;

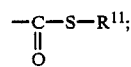

$-COR^{12}$; $-CHO$;

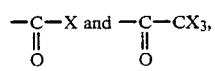

wherein X is halogen, and wherein $R^{11}$ and $R^{12}$ are independently selected from the group consisting of $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl and substituted benzyl, wherein the substituted phenyl and substituted benzyl are substituted with one or more substituents, each of said substituents being independently selected from the group consisting of $C_1$ to $C_6$ alkyl, methoxy and hydroxy, with the proviso that in a compound of the formula XI at least one of $R^1$, $R^3$, $R^6$ and $R^7$ is an amide, a nitrile, a carboxylic acid, a carboxylic acid ester, or a salt of a carboxylic acid, and with the provisos that in a compound of the formula XX at least one of $R^2$, $R^3$, $R^6$ and $R^7$ is an amide, a nitrile, a carboxylic acid, a carboxylic acid ester, or a salt of a carboxylic acid, and that $R^6$ cannot be $-COOH$ or $C\equiv N$ or $CONH_2$ when $R^2$, $R^3$ and $R^7$ are hydrogen.

15. A compound selected from the group consisting of compounds of the formulae VIII, IX, X, XVIII and XIX,

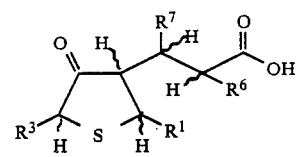

VIII

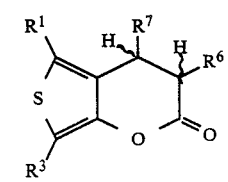

X

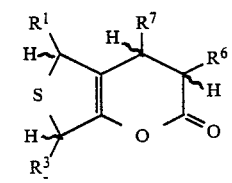

IX

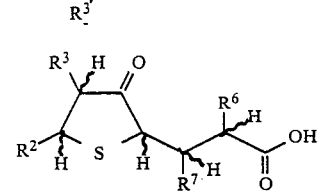

XVIII and

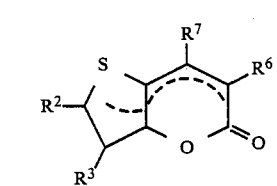

XIX wherein the broken line indicates that one double bond is present in the formula, and wherein $R^1$, $R^2$, $R^3$, $R^6$ and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl; substituted benzyl; wherein the substituted phenyl and substituted benzyl are substituted with one or more substituents, each of said substituents being independently selected from the group consisting of $C_1$ to $C_6$ alkyl, methoxy and hydroxy; $-C\equiv N$; $COOR^8$; wherein $R^8$ is selected from the group consisting of $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents, each of said substituents being independently selected from the group consisting of $C_1$ to $C_6$ alkyl, methoxy and hydroxy; —$CONR^9R^{10}$, wherein $R^9$ and $R^{10}$ are independently selected from the group consisting of hydrogen, $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents, each of said substituents being independently selected from the group consisting of $C_1$ to $C_6$ alkyl, methoxy and hydroxy, or $R^9$ and $R^{10}$ taken together with the nitrogen to which they are attached form an N-methyl piperazino, morpholino, piperidino, or pyrrolidino ring;

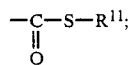

—$COR^{12}$; —CHO;

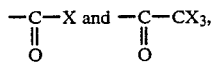

wherein X is halogen, and wherein $R^{11}$ and $R^{12}$ are independently selected from $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, and substituted benzyl, wherein the substituted phenyl and substituted benzyl are substituted with one or more substituents, each of said substituents being independently selected from the group consisting of $C_1$ to $C_6$ alkyl, methoxy and hydroxy.

16. A compound selected from the group consisting of compounds of the formulae XXI and XXII,

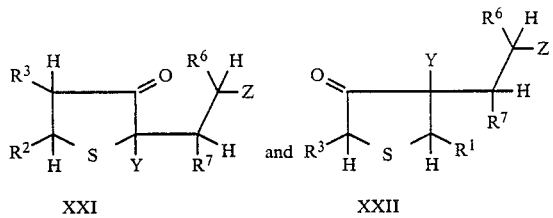

wherein $R^1$, $R^2$, $R^3$, $R^6$ and $R^7$ are independently selected from the group consisting of: hydrogen; $C_1$ to $C_6$ alkyl; $C_1$ to $C_6$ alkoxy-$C_1$ to $C_6$ alkyl; $C_3$ to $C_{12}$ cycloalkyl; phenyl; benzyl; substituted phenyl and substituted benzyl, wherein the substituted phenyl and substituted benzyl are substituted with one or more substituents, each of said substituents being independently selected from the group consisting of $C_1$ to $C_6$ alkyl, methoxy and hydroxy; —C≡N; $COOR^8$, wherein $R^8$ is selected from the group consisting of $C_1$ to $C_6$ alkyl, $C_1$ to $C_6$ alkoxy$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents, each of said substituents being independently selected from the group consisting of $C_1$ to $C_6$ alkyl, methoxy and hydroxy; —$CONR^9R^{10}$, wherein $R^9$ and $R^{10}$ are independently selected from the group consisting of hydrogen, $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents, each of said substituents being independently selected from the group consisting of $C_1$ to $C_6$ alkyl, methoxy and hydroxy, or $R^9$ and $R^{10}$ taken together with the nitrogen to which they are attached form an N-methyl piperazino, morpholino, piperidino, or pyrrolidino ring;

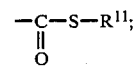

—$COR^{12}$; —CHO;

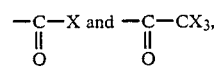

wherein X is halogen, and wherein $R^{11}$ and $R^{12}$ are independently selected from $C_1$ to $C_6$ alkyl, $C_1$ to $C_6$ alkoxy-$C_1$ to $C_6$ alkyl, $C_3$ to $C_{12}$ cycloalkyl, phenyl, benzyl, substituted phenyl, substituted benzyl, wherein the substituted phenyl and substituted benzyl are substituted with one or more substituents, each of said substituents being independently selected from the group consisting of $C_1$ to $C_6$ alkyl, methoxy and hydroxy, and wherein Z and Y are independently selected from the group consisting of —C≡N, —$COOR^{13}$, —$CONR^{14}R^{15}$, wherein $R^{13}$, $R^{14}$ and $R^{15}$ are independently selected from the group consisting of hydrogen, $C_1$ to $C_6$ alkyl, $C_1$ to $C_6$ alkoxy-$C_1$ to $C_6$ alkyl, $C_3$ to $CH_{12}$ cycloalkyl, phenyl, benzyl, substituted phenyl, substituted benzyl, wherein the substituted phenyl and substituted benzyl are substituted with one or more substituents, each of said substituents being independently selected from the group consisting of $C_2$ to $C_6$ alkyl, methoxy and hydroxy, or and $R^{14}$ and $R^{15}$ taken together with the nitrogen to which they are attached form an N-methyl piperazino, morpholino, piperidino, or pyrrolidino ring.

* * * * *

UNITED STATES PATENT AND TRADEMARK OFFICE
CERTIFICATE OF CORRECTION

PATENT NO. : 4,974,609              Page 1 of 3

DATED : December 4, 1990

INVENTOR(S) : Southwick et al.

It is certified that error appears in the above-identified patent and that said Letters Patent is hereby corrected as shown below:

Title page: Other Publications, line 3, change "Hramatka" to --Hromatka--

Column 2, line 46, insert --$R^{10}$-- between "and" and "are"

Column 5, line 44, change "$R^11$" to --$R^{11}$--

Column 5, line 44, insert --$R^{12}$-- after "and"

Column 10, line 35, change "$C_2Cl_2$" to --$CH_2Cl_2$--

Column 11, line 15, change "$C_2$" to --$Cl_2$--

Column 13, line 12, change "2methoxy" to --2-methoxy--

Column 13, line 51, change "$H_{2O}$" to --$H_2O$--

Column 14, line 5, delete second "$R^3$"

Column 14, line 16, change "$H_O$" to --$H_2O$--

Column 14, line 57, change "$C_2$" to --$CH_2$--

Column 14, line 67, change "HC" to --HCl--

Column 15, line 11, change "-5one" to -- -5-one--

UNITED STATES PATENT AND TRADEMARK OFFICE
CERTIFICATE OF CORRECTION

PATENT NO. : 4,974,609

DATED : December 4, 1990

INVENTOR(S) : Southwick et al.

It is certified that error appears in the above-identified patent and that said Letters Patent is hereby corrected as shown below:

Column 15, line 51, change "50R$^6$" to --=R$^7$--

Column 16, line 31, change "CH$_2$C$_{12}$" to --CH$_2$Cl$_2$--

Column 16, line 59, delete "b"

Column 17, line 51, change "$^{13.12}$" to --13.12--

Column 18, line 60, insert -- - -- betwen "2" and "b"

Column 19, line 8, change "12.5" to 112.5"

Column 19, line 16, change "55,43" to --55.43--

Column 21, line 33, change "CH$_6$" to --C$_6$--

Column 24, line 2, change "alkoxyC$_1$" to --alkoxy-C$_1$--

Column 24, line 45, change "CH$_{12}$" to --C$_{12}$--

UNITED STATES PATENT AND TRADEMARK OFFICE
CERTIFICATE OF CORRECTION

PATENT NO. : 4,974,609

DATED : December 4, 1990

INVENTOR(S) : Southwick et al.

It is certified that error appears in the above-identified patent and that said Letters Patent is hereby corrected as shown below:

Column 24, line 49, change "$C_2$" to --$C_1$--

Signed and Sealed this

Fourteenth Day of December, 1993

Attest:

BRUCE LEHMAN

Attesting Officer

Commissioner of Patents and Trademarks